United States Patent
Matsumiya (10) Patent No.: US 9,233,020 B2
(45) Date of Patent: Jan. 12, 2016

(54) CONTROLLER FOR VACUUM SUCTION TYPE URINE COLLECTOR

(75) Inventor: Rika Matsumiya, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 883 days.

(21) Appl. No.: 12/865,548

(22) PCT Filed: May 12, 2008

(86) PCT No.: PCT/JP2008/058696
§ 371 (c)(1),
(2), (4) Date: Nov. 30, 2010

(87) PCT Pub. No.: WO2009/037890
PCT Pub. Date: Mar. 26, 2009

(65) Prior Publication Data
US 2011/0064586 A1    Mar. 17, 2011

(30) Foreign Application Priority Data

Sep. 18, 2007    (JP) .................................. 2007-240363

(51) Int. Cl.
*E03D 11/00*    (2006.01)
*A47K 11/00*    (2006.01)
*A61F 5/451*    (2006.01)
*A61G 9/00*    (2006.01)

(52) U.S. Cl.
CPC ................ *A61F 5/451* (2013.01); *A61G 9/006* (2013.01)

(58) Field of Classification Search
CPC .... A61M 1/0031; A61M 1/0066; F04B 49/06
USPC ........................................ 4/431, 144.1, 144.2
See application file for complete search history.

(56) References Cited

U.S. PATENT DOCUMENTS

| | | | | |
|---|---|---|---|---|
| 4,531,939 | A | * | 7/1985 | Izumi .............................. 604/73 |
| 4,747,166 | A | * | 5/1988 | Kuntz ............................ 4/144.1 |
| 6,664,796 | B2 | * | 12/2003 | Wang et al. ................... 324/694 |
| 2001/0029435 | A1 | * | 10/2001 | Cocking et al. ................. 702/65 |

(Continued)

FOREIGN PATENT DOCUMENTS

JP    2006136492 A   *   6/2006

OTHER PUBLICATIONS

English machine translation of JP2006136492A.*

*Primary Examiner* — Huyen Le
*Assistant Examiner* — Christine Skubinna
(74) *Attorney, Agent, or Firm* — Wenderoth, Lind & Ponack, L.L.P.

(57) ABSTRACT

The conventional vacuum suction type urine collector may not be able to perform normal and automatic vacuum suction when contamination occurs between the electrodes acting as a sensor, and some users feel uneasy about the use of the urine collector as the case may be.

In the controller for a vacuum suction type urine collector of this invention, the resistance between paired electrodes installed on the side of a urine receiver on a vacuum sucked-urine path extending from the urine receiver via a urine transport tube to a urine tank is measured by a controller to automatically detect urine, for actuating a vacuum suction device, wherein a detection resistor is connected in series to the abovementioned electrodes; and a manual operation switch is connected in parallel to the series circuit consisting of the electrodes and the detection resistor, to constitute a state detection circuit.

10 Claims, 10 Drawing Sheets

(56) References Cited

U.S. PATENT DOCUMENTS

| | | | |
|---|---|---|---|
| 2005/0070861 A1* | 3/2005 | Okabe et al. | 604/327 |
| 2005/0247330 A1* | 11/2005 | Land et al. | 134/113 |
| 2008/0091153 A1* | 4/2008 | Harvie | 604/318 |
| 2008/0185399 A1* | 8/2008 | Yang et al. | 222/52 |
| 2008/0215220 A1* | 9/2008 | Winkel et al. | 701/68 |
| 2011/0060299 A1* | 3/2011 | Wada et al. | 604/318 |

* cited by examiner

CONTROLLER FOR VACUUM SUCTION TYPE URINE COLLECTOR

TECHNICAL FIELD

The present invention relates to a controller for a vacuum suction type urine collector in which the resistance between paired electrodes installed on the side of a urine receiver on a vacuum sucked-urine path extending from the urine receiver via a urine transport tube to a urine tank is measured by a control operation means, to automatically detect urine, for actuating a vacuum suction device.

BACKGROUND ART

A vacuum suction type urine collector as described above is conventionally proposed as shown, for example, in Patent Document 1. In the urine collector of Patent Document 1, a urine outlet is formed on the rear side of a urine receiver having a urine suction opening formed, on the front side, to be applied to a urinating region; a urine transport tube communicating with a urine tank is connected with the urine outlet; a vacuum suction device is connected with the top of the urine tank; paired electrodes are installed with a distance kept between them at the urine outlet; and the urine discharged from the urine suction opening into the urine receiver lowers the resistance between the aforementioned paired electrodes, when the vacuum suction device is actuated to vacuum-suck the urine.

Patent Document 1; Microfilm of Japan Patent Application No. 55-033371

DISCLOSURE OF THE INVENTION

Problem to be Solved by the Invention

The conventional vacuum suction type urine collector as described above has the following problems.
1. The sole means for actuating the vacuum suction device to initiate the vacuum suction of urine is the sensor consisting of the paired electrodes, and if the electrodes are contaminated to constantly decline in resistance, the decline of resistance due to urine cannot be identified not allowing the normal vacuum suction of urine.
2. Some users doubt that the automatic vacuum suction of urine can be actually performed, and fear that the urine collector may cause leakage and overflowing, hesitating to use the automatic urine collector.

The object of this invention is to solve the abovementioned problems.

Means for Solving the Problems

To achieve the above object, this invention proposes a controller for a vacuum suction type urine collector in which the resistance between paired electrodes installed on the side of a urine receiver on a vacuum sucked-urine path extending from the urine receiver via a urine transport tube to a urine tank is measured by a controller, to automatically detect urine, for actuating a vacuum suction device, wherein a detection resistor is connected in series to the abovementioned electrodes; and a manual operation switch is connected in parallel to the series circuit consisting of the electrodes and the detection resistor, to constitute a state detection circuit.

Further, this invention proposes the abovementioned configuration, wherein the controller comprises a resistance measuring means of the state detection circuit, a classifying means for classifying the resistance measured by the resistance measuring means as the corresponding one of established multiple resistance classes, a class storing means for storing the corresponding resistance class, a class change detecting means for detecting the change of class by comparing the corresponding resistance class identified by the classifying means with the corresponding resistance class stored in the class storing means, an action mode setting means for setting the action mode in reference to the change of class detected by the class change detecting means and to the state of the manual operation switch detected from the resistance of the state detection circuit, and a control operation means for controlling the vacuum suction device on the basis of the set action mode.

Further, this invention proposes the abovementioned configuration, wherein the action mode to be set is either a manual operation-based action mode where the manual operation switch is turned on or a urine detection-based action mode where the manual operation switch is turned off.

Further, this invention proposes the abovementioned configuration, wherein the resistance classes include a normal class of a high resistance range corresponding to a state substantially free from the contamination between the electrodes, an alarm class of a low resistance range corresponding to a state where it is difficult to detect urine in reference to the resistance only because of the large contamination between the electrodes, and an appropriate number of intermediate classes corresponding to the states between the normal class and the alarm class; and the control operation means issues a contamination alarm in the case where the resistance class identified by the classifying means while the power of the urine collector is switched on is the alarm class.

Further, this invention proposes the abovementioned configuration, wherein the resistance classes include a normal class of a high resistance range corresponding to a state substantially free from the contamination between the electrodes, an alarm class of a low resistance range corresponding to a state where it is difficult to detect urine in reference to the resistance only because of the large contamination between the electrodes, and an appropriate number of intermediate classes corresponding to the states between the normal class and the alarm class; and the action mode setting means sets the urine detection-based action mode when the change from another class to the alarm class is detected, and cancels the urine detection-based action mode when the change from the alarm class to another class is detected, for actuating the control operation means.

Further, this invention proposes the abovementioned configuration, wherein the control operation means is provided with a timer means, to ensure that the action of the vacuum suction device is stopped after the lapse of a set time period ($\beta$) from the time point when the urine detection-based action mode is cancelled.

Further, this invention proposes the abovementioned configuration, wherein the set time period ($\beta$) is set as a coefficient multiple of the elapsing time period ($\alpha$) from the time point when the urine detection-based action mode is set to the time point when the urine detection-based action mode is cancelled.

Further, this invention proposes the abovementioned configuration, wherein the control operation means is provided with a timer means, to ensure that in the case where the elapsing time period from the time point when the urine detection-based action mode is set has exceeded a set time period ($\delta$), a sensor contamination alarm is issued and the action of the vacuum suction device is stopped.

Further, this invention proposes the abovementioned configuration, wherein the control operation means is provided with a timer means, to ensure that after the lapse of a set time period ($\phi$) from the time point when the manual operation-based action mode is set with the manual operation switch turned on, the action of the vacuum suction device is stopped.

Further, this invention proposes the abovementioned configuration, wherein the control operation means is provided with a timer means, to ensure that in the case where the manual operation switch is turned on again before the set time period ($\phi$) elapses from the time point when the manual operation-based action mode is set with the manual operation switch turned on, the action of the vacuum suction device is stopped after the lapse of a set time period ($\gamma$) from the time point when the manual operation switch is turned on again.

Further, this invention proposes the abovementioned configuration, wherein at the time point when the set time period ($\gamma$) has elapsed, the control operation means refers to the class of the resistance of the state detection circuit at the time point, and if the class is the alarm class, shifting to the urine detection-based action mode occurs, and if the class is other than the alarm class, the vacuum suction device is stopped.

Further, this invention proposes the abovementioned configuration, wherein at the time point when the set time period ($\gamma$) has elapsed, the control operation means refers to the class of the resistance of the state detection circuit at the time point and to the resistance class stored in the class storing means, and in the case where the stored resistance class is other than the alarm class, if the resistance class at the time point is the alarm class, shifting to the urine detection-based action mode occurs, and if the resistance class at the time point is other than the alarm class, the vacuum suction device is stopped; and in the case where the stored resistance class is the alarm class, the vacuum suction device is stopped.

Further, this invention proposes the abovementioned configuration, wherein in the urine detection-based action mode, the control operation means actuates the vacuum suction device in such a manner as to make the suction force high, and in the manual operation-based action mode, the control operation means actuates the vacuum suction device in such a manner as to make the suction force lower than that in the urine detection-based action mode.

Further, this invention proposes the abovementioned configuration, wherein in the manual operation-based action mode, the control operation means actuates the vacuum suction device in such a manner as to make the suction force high in the case where the resistance class till then is the alarm class.

Effects of the Invention

In the state detection circuit of this invention described above, in the state where the manual operation switch is turned off, the resistance measuring means of the controller measures the resistance of the series circuit consisting of the paired electrodes and the detection resistor, and therefore detects the decline of the resistance by the urine existing between the paired electrodes, to detect urine. Thus, the vacuum suction device is actuated in the urine detection-based action mode, to automatically suck urine for collection into the urine tank. Further, if the urination ends to raise the resistance between the paired electrodes, it is detected to automatically stop the vacuum suction device.

The resistance measuring means of the controller measures the resistance of the series circuit consisting of the paired electrodes and the detection resistor. Since the resistance of the detection resistor is known, if the known resistance is subtracted from the measured resistance, the resistance between the paired electrodes can be obtained.

If urination ends and the resistance between the paired electrodes rises, then the vacuum suction device is stopped after the lapse of the set time period ($\beta$) corresponding to a turning-off delay time period, to ensure that all the urine in the urine transport tube can be discharged into the urine tank.

As the set time period ($\beta$), the elapsing time period ($\alpha$) from the time point when the urine detection-based action mode is set to the time point when urine is not detected any more is multiplied by a coefficient (c), for example, a number smaller than 1 such as ½, to calculate the set time period ($\beta$) from formula $\beta = c \times \alpha$. By setting the time period, all the urine in the urine transport tube can be reliably discharged into the urine tank, and it can be prevented that the vacuum suction device is actuated for a period longer than necessary.

In the case where the urine detection state continues also after a very long period has elapsed from the time point when the vacuum suction device is actuated on the basis of detected urine, it can be considered that the resistance is kept low owing to the contamination between the electrodes. Therefore, in this invention, in the case where the abovementioned elapsing time period exceeds the set time period ($\delta$), a contamination alarm is issued, and the vacuum suction device is stopped. Thus, the inconvenience that the vacuum suction device cannot be stopped due to the contamination between the electrodes can be prevented.

Then, if the manual operation switch is turned on, the resistance of the state detection circuit measured by the resistance measuring means of the controller becomes 0. On the other hand, the resistance of the state detection circuit measured by the resistance measuring means of the controller with the manual operation switch turned off is the resistance of the series circuit consisting of the paired electrodes and the detection resistor. Therefore, even if the resistance by the urine between the paired electrodes becomes 0 or declines to near 0 owing to contamination, the measured resistance is equal to or higher than the resistance of the detection resistor.

Consequently in this invention, the decline of resistance of the state detection circuit with the manual operation switch turned on and the decline of resistance of the state detection circuit by the decline of resistance between the paired electrodes by urine with the manual operation switch turned off can be clearly and reliably distinguished, and therefore the action mode can be reliably set and the vacuum suction device can be reliably actuated in the set action mode.

In the manual operation-based action mode where the manual operation switch is turned on, the action of the vacuum suction device is stopped after the lapse of the set time period ($\phi$) from the time point when the action of the manual operation-based action mode is initiated with the manual operation switch turned on, so that the action of the vacuum suction device can be stopped without operating the manual operation switch, etc.

If the set time period ($\phi$) is set at an appropriate value longer than the supposed longest urination time period, all the urine can be discharged into the urine tank.

Further in the manual operation-based action mode, the second operation of turning on the manual operation switch can be used as a urination end signal. That is, in this invention, in the case where the manual operation switch is turned on again while urination is performed after the manual operation switch is turned on before urination, the action of the vacuum suction device can be stopped after lapse of $\gamma$ seconds from the time point when the switch is turned on second time.

If the second operation of turning on the manual operation switch is performed at the time point when urination ends, the action of the vacuum suction device can be stopped after the lapse of a sufficient time period, that is, after the lapse of the set time period γ for allowing all the urine to be discharged into the urine tank after the end of urination.

With regard to this action, in the case where urination ends within a time period very shorter than the set time period φ, if the manual operation switch is turned on second time as described above, the action of the vacuum suction device can be stopped at a time point earlier than the time point when the predetermined time period φ elapses, to inhibit the wasteful action of the vacuum suction device.

For allowing the abovementioned actions, in this invention, as described before, the controller comprises a resistance measuring means of the state detection circuit, a classifying means for classifying the resistance measured by the resistance measuring means as the corresponding one of established multiple resistance classes, a class storing means for storing the corresponding class of the resistance, a class change detecting means for detecting the change of class by comparing the resistance class identified by the classifying means with the resistance class stored in the class storing means, an action mode setting means for setting the action mode in reference to the change of class detected by the class change detecting means and to the state of the manual operation switch detected from the resistance of the state detection circuit, and a control operation means for controlling the vacuum suction device on the basis of the set action mode. These respective means can be provided by a computer.

The action mode to be set is either a manual operation-based action mode where the manual operation switch is turned on and a urine detection-based action mode where the manual operation switch is turned off. The resistance classes include a normal class of a high resistance range corresponding to a state substantially free from the contamination between the electrodes, an alarm class of a low resistance range corresponding to a state where it is difficult to detect urine in reference to the resistance only because of the large contamination between the electrodes, and an appropriate number of intermediate classes corresponding to the states between the normal class and the alarm class.

In this configuration, when the action mode setting means detects the change from another class to the alarm class, it can set the urine detection-based action mode for actuating the vacuum suction device, and when the action mode setting means detects the change from the alarm class to another class, it can cancel the urine detection-based action mode, for stopping the vacuum suction device.

Further, in the case where the resistance class at the time point when the power of the urine collector is turned on is the alarm class, or in the case where a urine-detected state has passed the set time period (δ) after change from another class to the alarm class, the controller can detect the case concerned, for allowing a contamination alarm to be issued.

Further in this invention, as described above, at the time point when the set time period (γ) or (φ) has elapsed after start of the action of the vacuum suction device in the action of the manual operation-based action mode, the class of the resistance of the state detection circuit at that time point can be referred to, and if the class is the alarm class, the action mode can be shifted to the urine detection-based action mode, and if the class is other than the alarm class, the vacuum suction device can be stopped.

In this configuration, even if urination does not end at the time point when the set time period (γ) or (φ) of the manual operation-based action mode has elapsed when the action of the vacuum suction device should be stopped as described above, all the urine can be reliably discharged into the urine tank in the urine detection-based action mode.

The abovementioned shift from the manual operation-based action mode to the urine detection-based action mode can be enforced only in the case where the resistance class stored in the class storing means is other than the alarm class.

This configuration is intended to prevent the following wasteful action. In the case where the resistance class is the alarm class, if the action in the manual operation-based action mode is performed with the manual operation switch turned on, it is evident that if the mode is shifted to the urine detection-based action mode, the action continues still after the elapsing time period of the action exceeds the set time period (δ) till the vacuum suction device stops.

Further in this invention, in the urine detection-based action mode, the vacuum suction device can be actuated in such a manner as to make the suction force high, and in the manual operation-based action mode, the vacuum suction device can be actuated in such a manner as to make the suction force lower than that in the urine detection-based mode.

In this configuration, since it is highly probable that urine does not exist between the electrodes in the manual operation-based action mode, the operation can be performed with the suction force of the vacuum suction device kept low, and in this operation, the action sound such as suction sound can be decreased. Further, since it is highly probable that urine exists between the electrodes in the urine detection-based action mode, the vacuum suction device can be operated with a high suction force for allowing reliable suction of urine.

Further in the above configuration, in the manual operation-based action model, if the resistance class till then is the alarm class, the vacuum suction device can be actuated in such a manner as to make the suction force high.

In this configuration, in the manual operation-based action mode, if the resistance class till then is the alarm class, it is highly probable that at the time point when the manual operation switch is turned on, urine already reaches the electrodes. Therefore, even in the manual operation-based action mode, the vacuum suction device can be actuated in such a manner as to make the suction force high for allowing reliable suction of urine.

MEANINGS OF SYMBOLS 1 urine receiver
2 urine suction opening
3 handle
4 urine outlet
5 vent hole
6 state detecting section
7 urine transport tube
8 urine tank
9 vacuum suction device
10 vacuum suction tube
11 a pair of electrodes
12 detection resistor
13 manual operation switch
14 state detection circuit
15 controller
16 signal line
17 resistance measuring means
18 classifying means
19 class storing means
20 class change detecting means
21 action mode setting means
22 control operation means
23 water level sensor

THE BEST MODES FOR CARRYING OUT THE INVENTION

Figure 1:
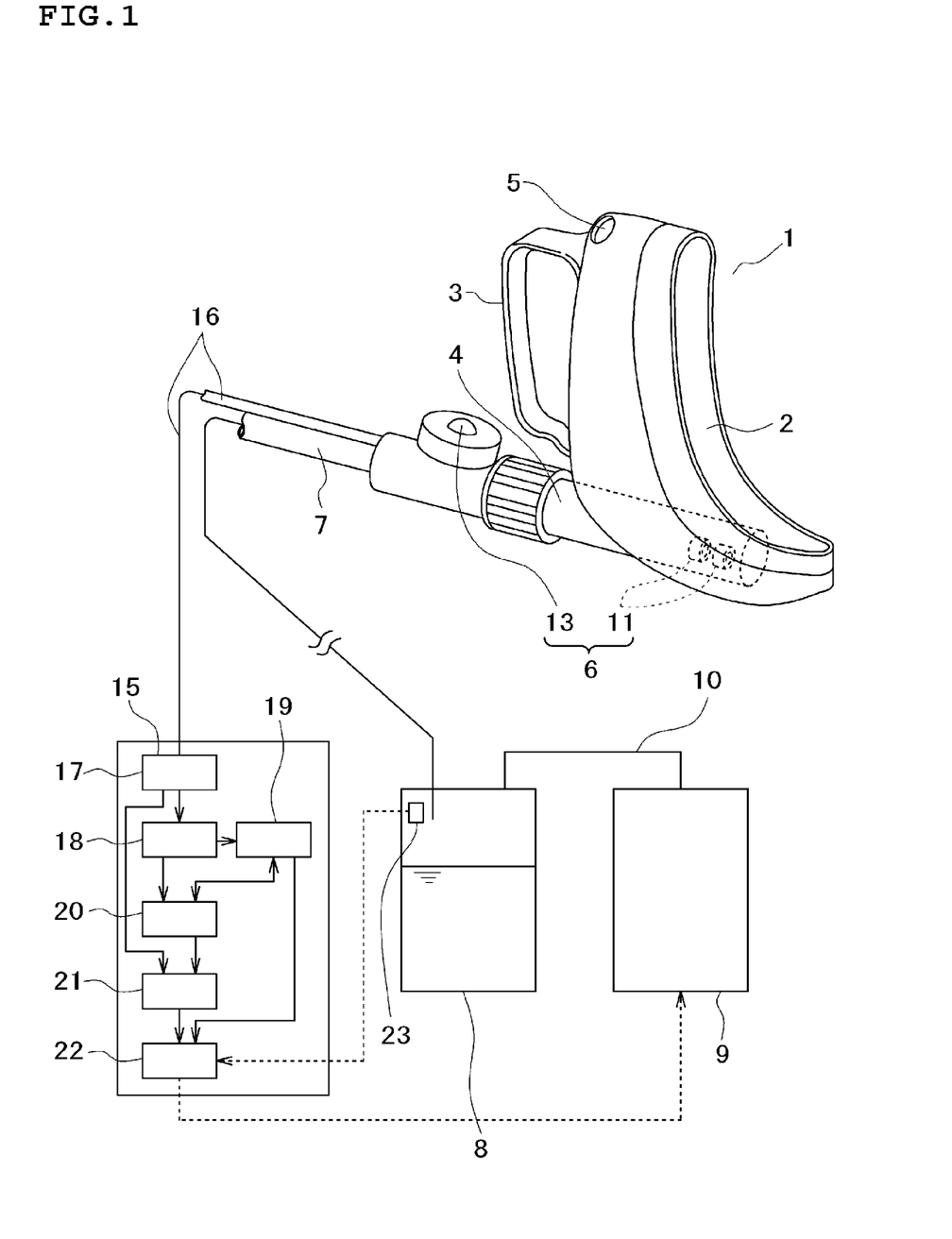
FIG. 1 is an illustration conceptually showing the entire configuration of an embodiment of the controller for a vacuum suction type urine collector of this invention.
Figure 2:
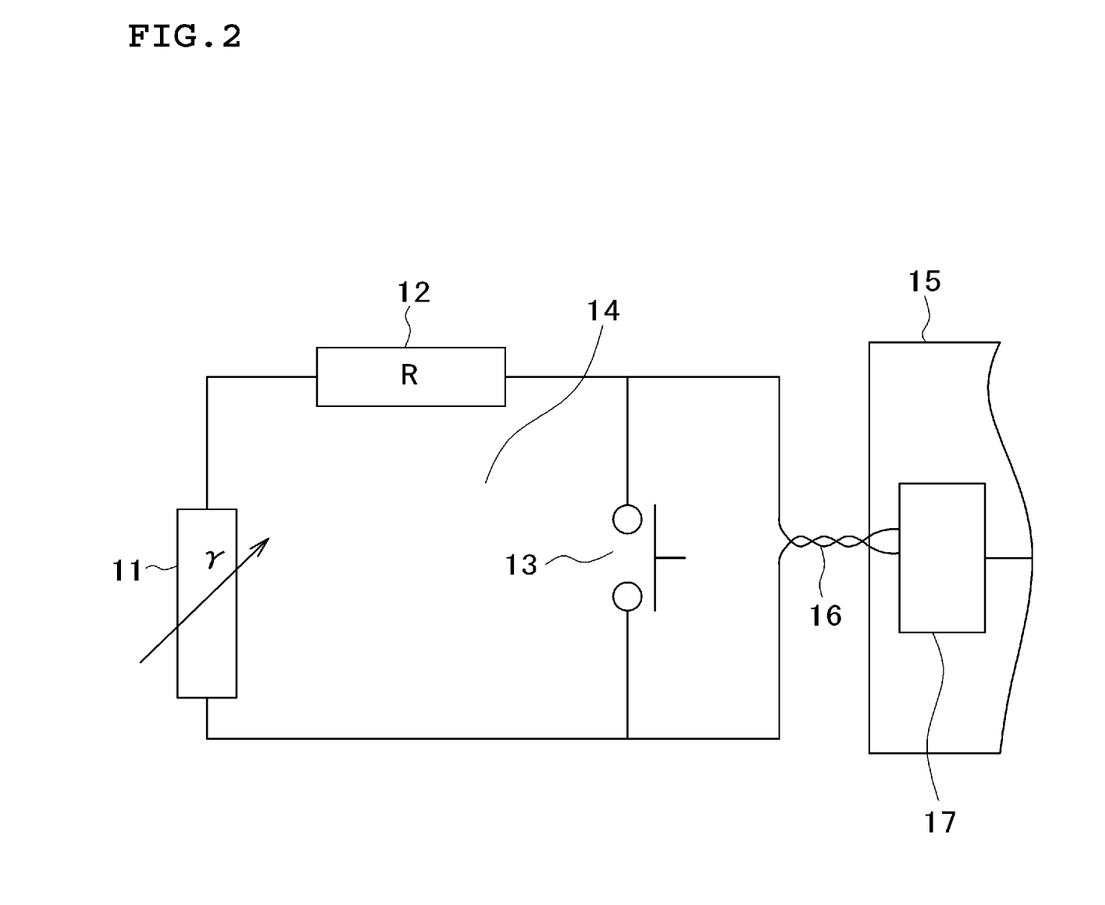
FIG. 2 is an illustration showing an essential portion.

Modes for carrying out this invention are explained below in reference to the attached drawings. At first, FIG. 1 is an illustration conceptually showing the entire configuration of an embodiment of the vacuum suction type urine collector of this invention, and FIG. 2 is an illustration of an essential portion.

In the drawings, symbol 1 denotes a urine receiver for a female. The urine receiver 1 has a urine suction opening 2 formed on the front side and a handle 3 formed on the rear side, and has a urine outlet 4 formed at the bottom on the rear side and a vent hole 5 formed at the top on the rear side. The urine outlet 4 is connected with one end of a urine transport tube via a state detecting section 6, and the other end of the urine transport tube 7 is connected with the top of a urine tank 8. Symbol 9 denotes a vacuum suction device, and a vacuum suction tube 10 of the vacuum suction device 9 is connected with the top of the urine tank 8.

The state detecting section 6 is provided with a pair of electrodes 11 kept apart from each other, and a detection resistor 12 is connected in series to the electrodes 11, for constituting a series circuit, and a manual operation switch 13 is connected in parallel to the series circuit, to constitute a state detection circuit 14. The resistance between the paired electrodes is expressed as a variable resistor in FIG. 2, since the resistance varies depending on urine and other contamination, and the resistance is expressed as r. Further, the detection resistor 12 has a constant resistance which is expressed as R.

Symbol 15 denotes a controller, and the controller 15 comprises a resistance measuring means 17 connected with the state detection circuit 14 via a signal line 16, a classifying means 18 for identifying the class of the resistance measured by the resistance measuring means 17 among multiple established resistance classes, a class storing means 19 for storing the corresponding resistance class, a class change detecting means 20 for detecting the change of class by comparing the resistance class identified by the classifying means and the resistance class stored by the class storing means 19, an action mode setting means 21 for setting the action mode in reference to the change of class detected by the class change detecting means 20 and to the state of the manual operation switch 13 detected from the resistance of the state detection circuit 14 measured by the resistance measuring means 17, and a control operation means 22 for controlling the vacuum suction device 9 on the basis of the set action mode. Symbol 23 denotes a water level sensor.

In the above configuration, in the state where the manual operation switch 13 is turned off, the resistance measuring means 17 of the controller 15 measures the resistance of the series circuit consisting of the paired electrodes 11 and the detection resistor 12, hence detects the decline of resistance by the urine existing between the paired electrodes 11, to detect urine, as described later in detail. Thus, the vacuum suction device 9 can be actuated in the urine detection-based action mode, to automatically suck urine into the urine tank 8, for urine collection. Subsequently if the urination ends and the resistance between the paired electrodes 11 rises, then the urination end can be detected to automatically stop the vacuum suction device 9.

In this embodiment, in the state where the manual operation switch 13 is turned on, the resistance of the state detection circuit 14 measured by the resistance measuring means 17 is 0. Therefore, the action mode setting means 21 that receives this signal sets the manual operation-based action mode as the action mode, and outputs it to the control operation means 22. The control operation means 22 controls the vacuum suction device 9 on the basis of the manual operation-based action mode.

On the other hand, in the state where the manual operation switch 13 is turned off, the resistance measuring means 17 measures the resistance of the series circuit consisting of the paired electrodes 11 and the detection resistor 12, and therefore, detects the decline of resistance caused by the urine existing between the paired electrodes 11, to detect urine. Thus, as described later in detail, the vacuum suction device 9 is actuated in the urine detection-based action mode, to automatically suck urine into the urine tank 8, for urine collection. Then, if the urination ends and the resistance between the paired electrodes 11 rises, then the urination end can be detected to automatically stop the vacuum suction device 9.

As described above, the resistance measuring means 17 measures the resistance of the series circuit consisting of the paired electrodes 11 and the detection resistor 12. Since the resistance R of the detection resistor 12 is known, if the known resistance R is decreased from the measured resistance, the resistance between the paired electrodes 11 can be obtained.

The resistance measured by the resistance measuring means 17 is classified as the corresponding one of established multiple resistance classes by the classifying means 18. For example, in this embodiment, the resistance is classified as the corresponding one of the following four classes (class A to class D) in response to the degree of contamination between the electrodes 11, and the corresponding class is stored in the class storing means 19.

| | |
|---|---|
| Class A: Normal (no contamination) | $r > Ra$ |
| Class B: Little contamination | $Ra \geq r > Rb$ |
| Class C: Medium contamination | $Rb \geq r > Rc$ |
| Class D: Much contamination | $Rc \geq r > 0$ | where Ra>Rb>Rc>0

In the above, class D is the alarm class, and in the case where the resistance is classified as class D by the classifying means 18, the information is transmitted via the class storing means 19 to the control operation means 22 as indicated by arrows in FIG. 1, for letting the control operation means 22 issue an alarm.

The measurement of the resistance of the state detection circuit 14 by the resistance measuring means 17 is performed continuously to monitor the change of resistance.

That is, the resistance, is measured by the resistance measuring means 17 and classified by the classifying means 18 as the corresponding one of established multiple resistance classes, and the corresponding class is stored by the class storing means 19. When a certain time period has elapsed after the storing of the corresponding class, the resistance is measured again by the resistance measuring means 17 and classified by the classifying means 18. The stored corresponding class and the newly identified corresponding class are compared by the class change detecting means 20, to detect any change.

As a result of the comparison by the class change detecting means 20, if the newly identified corresponding class is class D while the stored corresponding class is class A, B or C, the class stored in the class storing means 19 is replaced by class D, and the result is outputted to the action mode setting means 21. The action mode setting means 21 outputs a signal for setting the urine detection-based action mode to the control operation means 22. Therefore, the control operation means 22 controls the vacuum suction device 9 on the basis of the predetermined sequence of the urine detection-based action mode.

To ensure that the abovementioned actions can be performed, the class storing means 19 can be made to store both the corresponding class newly identified by the classifying means 18 and the corresponding class previously identified by the classifying means 18, or the corresponding class stored by the class storing means 19 can be made to be replaced when the class change detecting means 20 detects the change of class.

On the other hand, as a result of comparison in the class change detecting means 20, if the newly identified corresponding class is class A, B or C and the stored corresponding class is class D, then the result is outputted to the action mode setting means 21, and the action mode setting means 21 outputs a signal for canceling the urine detection-based action mode to the control operation means 22. Therefore, the control operation means 22 stops the vacuum suction device 9 on the basis of the predetermined sequence of the urine detection-based action mode. Meanwhile, if the newly identified corresponding class used for delivering a signal for canceling the urine detection-based action mode is restricted to class A or B, to prevent the cancellation of the urine detection-based action mode when the newly identified corresponding class is class C, it can be reliably prevented that the urine remains in the urine transport tube.

The abovementioned actions and the actions in the urine detection-based action mode and the manual operation-based action mode are explained below in detail on the basis of the flowcharts shown in FIGS. 3 to 8 and the time charts shown in FIGS. 9 to 12.

Figure 3:
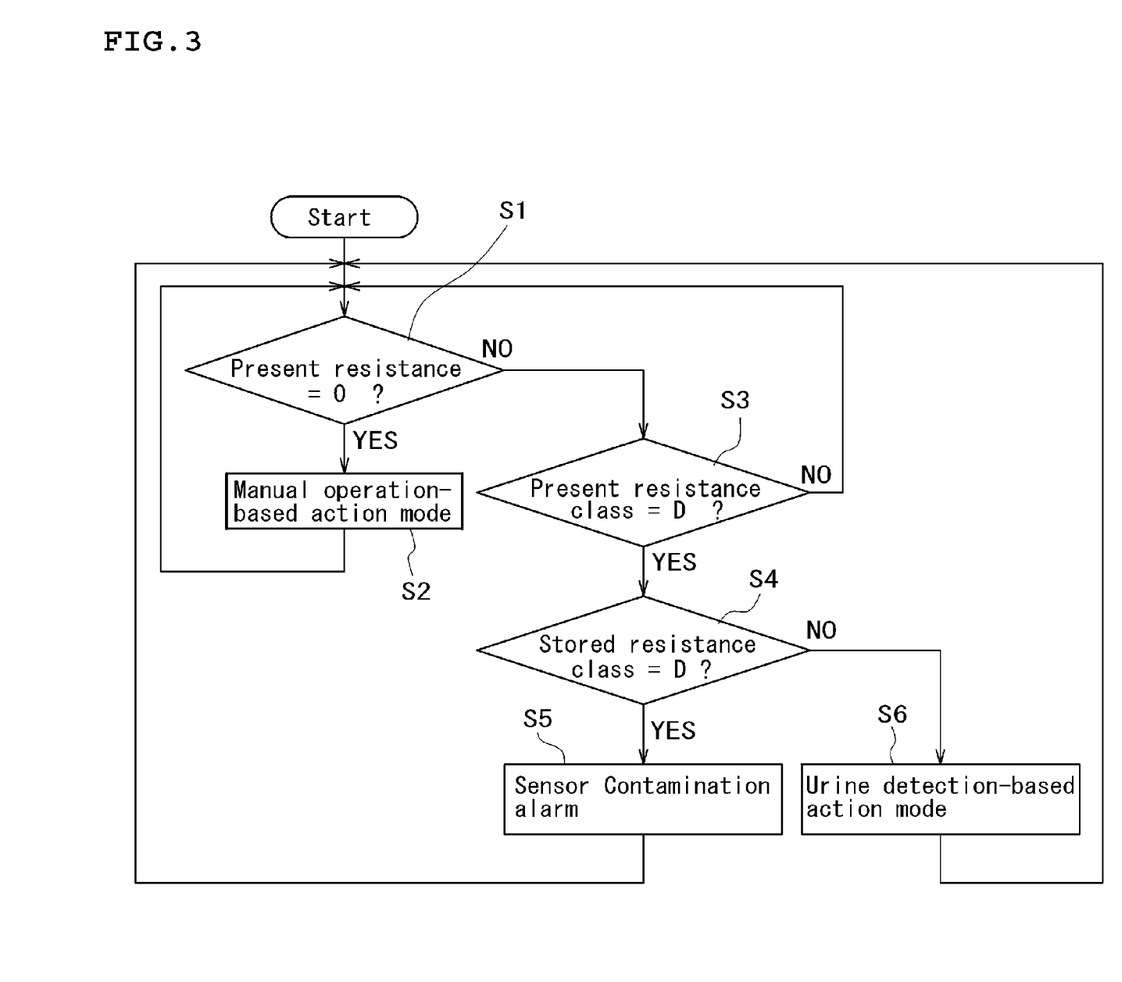
FIG. 3 is a flowchart showing an example of the entire flow of control in this invention.

At first, FIG. 3 shows the entire flow of control in this invention. If control is started by turning on the power, etc., the resistance measuring means 17 measures the present resistance of the state detection circuit 14, and at step S1, whether or not the resistance is 0, that is, whether or not the manual operation switch 13 has been turned on is judged.

If the resistance is 0, it is judged that the manual operation switch 13 has been turned on, and shifting to the manual operation-based action mode shown as step S2 occurs. The flow of control of the manual operation-based action mode is described later in detail in reference to FIGS. 4 to 7.

On the other hand, if the resistance is not 0 at step S1, it is judged that the manual operation switch 13 is turned off. In this case, shifting to step S3 occurs, and the present resistance class identified by the classifying means 18 is confirmed. That is, at step S3, whether or not the present resistance class is class D corresponding to the alarm class is judged, and if it is not class D, shifting to step S1 occurs to continue the observation of resistance in the standby state.

On the other hand, if the present resistance class is class D, shifting to step 4 occurs, and whether or not the resistance class stored in the class storing means 19 is class D is judged.

If the stored resistance class is class D, it is judged that the state of class D continues till now, and shifting from step S4 to step S5 occurs. At step S5, a sensor contamination alarm is issued to indicate that contamination occurs between the electrodes, and shifting to S1 occurs. In this case, shifting to neither the manual operation-based action mode nor the urine detection-based action mode occurs, and an alarm is merely issued to stay in the standby state.

That is, if the resistance class is class D corresponding to the alarm class due to the contamination between the electrodes, an alarm is issued, not allowing shifting to the urine detection-based action mode. However, if the manual operation switch 13 is turned on, shifting to the manual operation-based action mode is allowed. This flow of control is shown in the time chart of FIG. 12.

On the other hand, if the stored resistance class is not class D, it means that the state of class A, B or C has changed to the state of class D. Therefore, it is determined that urine exists between the electrodes, and shifting to the urine detection-based action mode shown as step S6 occurs. After completion of control in this mode, shifting to step S1 occurs. The flow of control in the urine detection-based action mode is described later in detail in reference to FIG. 8.

Figure 4:
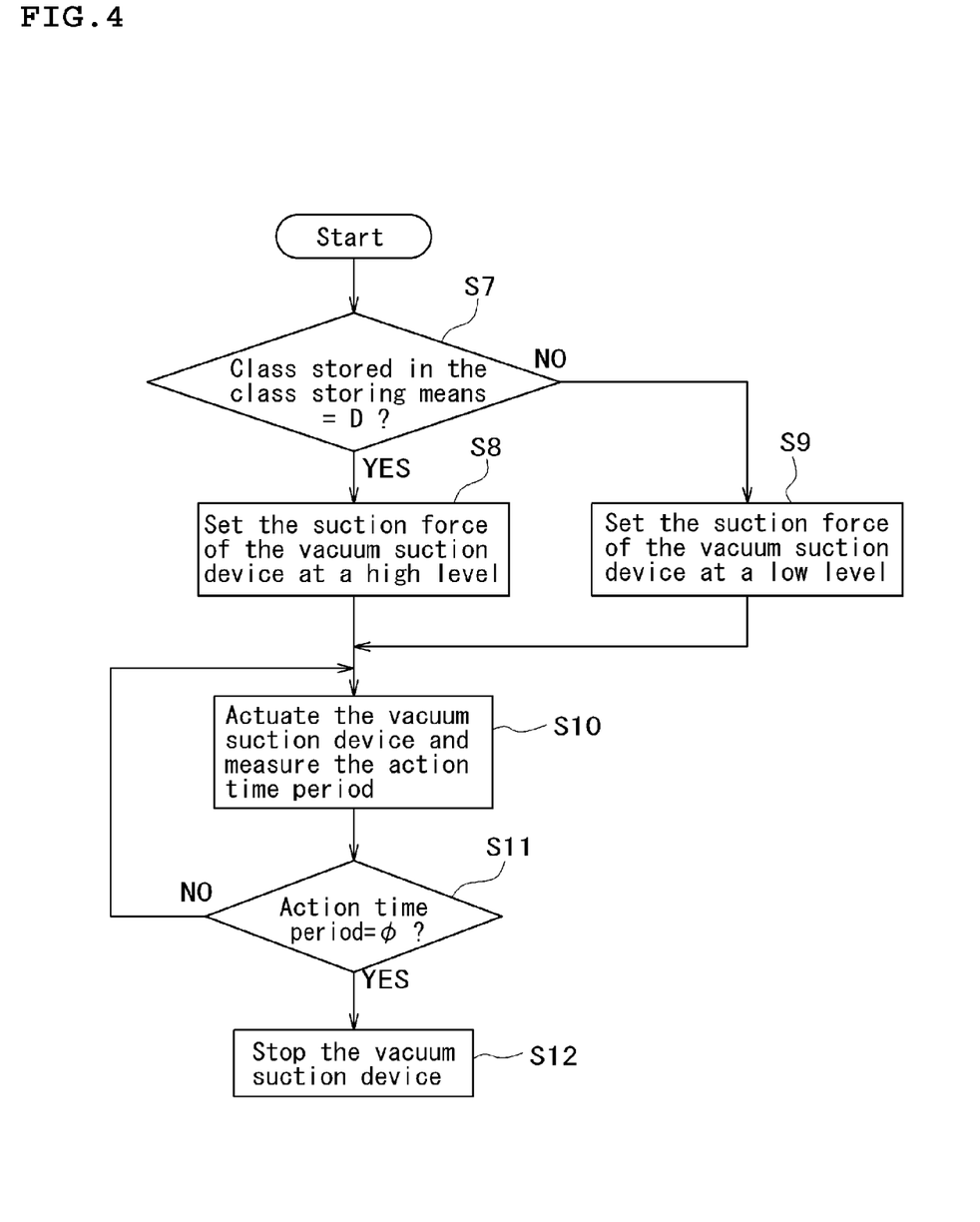
FIG. 4 is a flowchart showing an example of the flow of control in the manual operation-based action mode.

FIG. 4 shows an example of the flow of control in the manual operation-based action mode (S2).

If shifting from step S1 of FIG. 3 to the manual operation-based action mode (S2) occurs, at first, at step S7, whether or not the resistance class stored in the class storing means 19 is class D is judged.

If the stored resistance class is class D, it means that there is contamination between the electrodes. Therefore, even if urine exists there, it is difficult to detect urine. Since urine may already exist, shifting to step S8 occurs to set the suction force of the vacuum suction device 9 at a high level. On the other hand, if the stored resistance class is not class D but is class A, B or C, the existence of urine can be detected well. In this case, since the possibility that urine exists between the electrodes at the time point when the manual operation switch is turned on is low, shifting to step S9 occurs to set the suction force of the vacuum suction device 9 at a low level.

After the suction force of the vacuum suction device 9 is set at step S8 or S9, shifting to step S10 occurs to actuate the vacuum suction device 9 and to measure the action time period.

Then at step S11, whether or not the action time period has exceeded the set time period $\phi$ is judged, and if the action time period does not exceed the set time period $\phi$, shifting to S10 occurs to continue the action of the vacuum suction device 9 and the time period measurement. On the other hand, if the action time period has exceeded the set time period $\phi$, shifting to step S12 occurs to stop the vacuum suction device 9, for terminating the manual operation-based action mode (S2). After completion of the mode, shifting to step S1 occurs as shown in FIG. 3, and the observation of the resistance of the state detection circuit 14 is continued in the standby state.

In the abovementioned flow of control, on the basis of the judgment at step S7, shifting to either step S8 or S9 occurs to ensure that if the resistance class till then is class D, the vacuum suction device 9 is actuated at a high suction force or that if the resistance class till then is class A, B or C, the vacuum suction device 9 is actuated at a low suction force. However, as another example of control, without performing such adjustment of suction force, as soon as shifting to the manual operation-based action mode (S2) occurs, immediate shifting to step S10 may also be made to occur for ensuring the flow of control in which the vacuum suction device 9 is actuated at a preset suction force.

Figure 10:
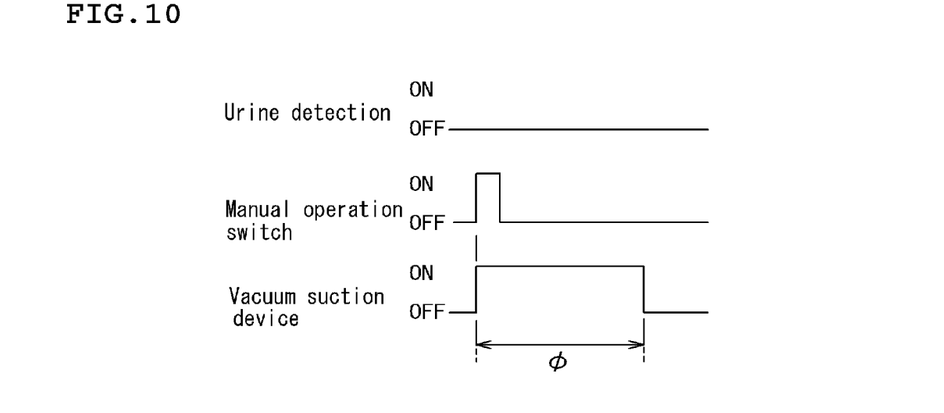
FIG. 10 is a time chart showing another part of the flow of control.
Figure 11:
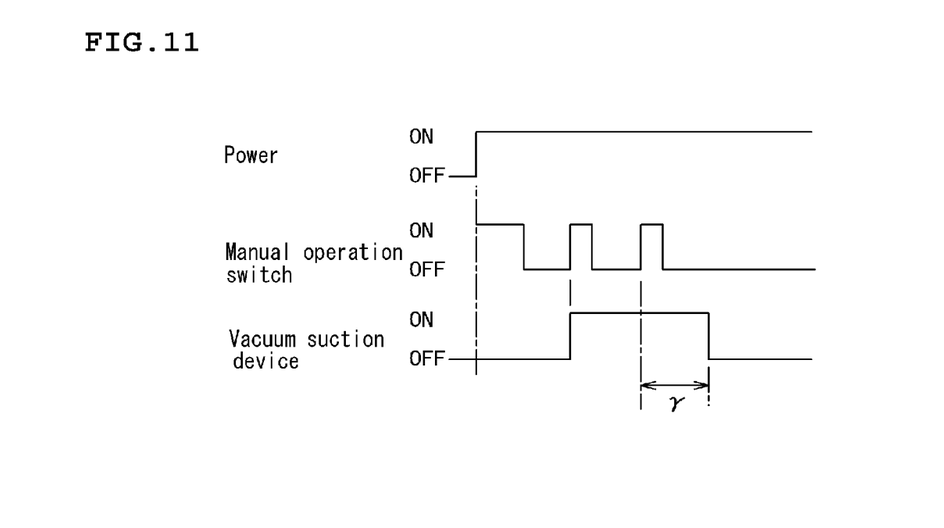
FIG. 11 is a time chart showing a further other part of the flow of control.
Figure 12:
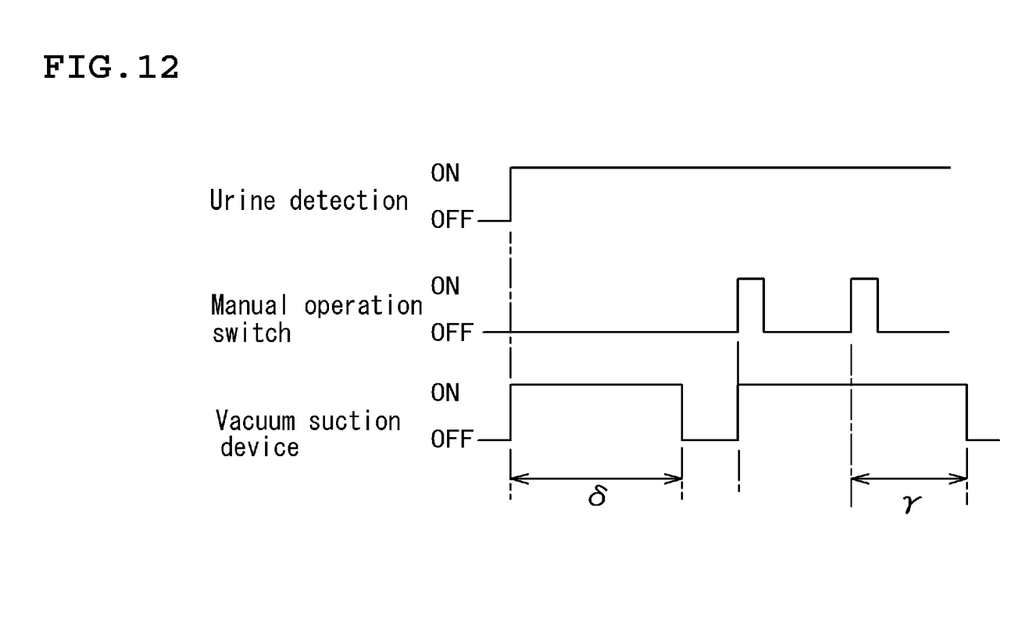
FIG. 12 is a time chart showing a further other part of the flow of control.

Anyway, in the manual operation-based action mode (S2) in the state where the manual operation switch 13 is turned on, as shown in the time chart of FIG. 10, if the action of the vacuum suction device 9 is stopped after the lapse of a set time period ($\phi$) from the time point when the action is started, the action of the vacuum suction device 9 can be automatically stopped without the operation to stop the manual operation switch 13, etc.

Figure 5:
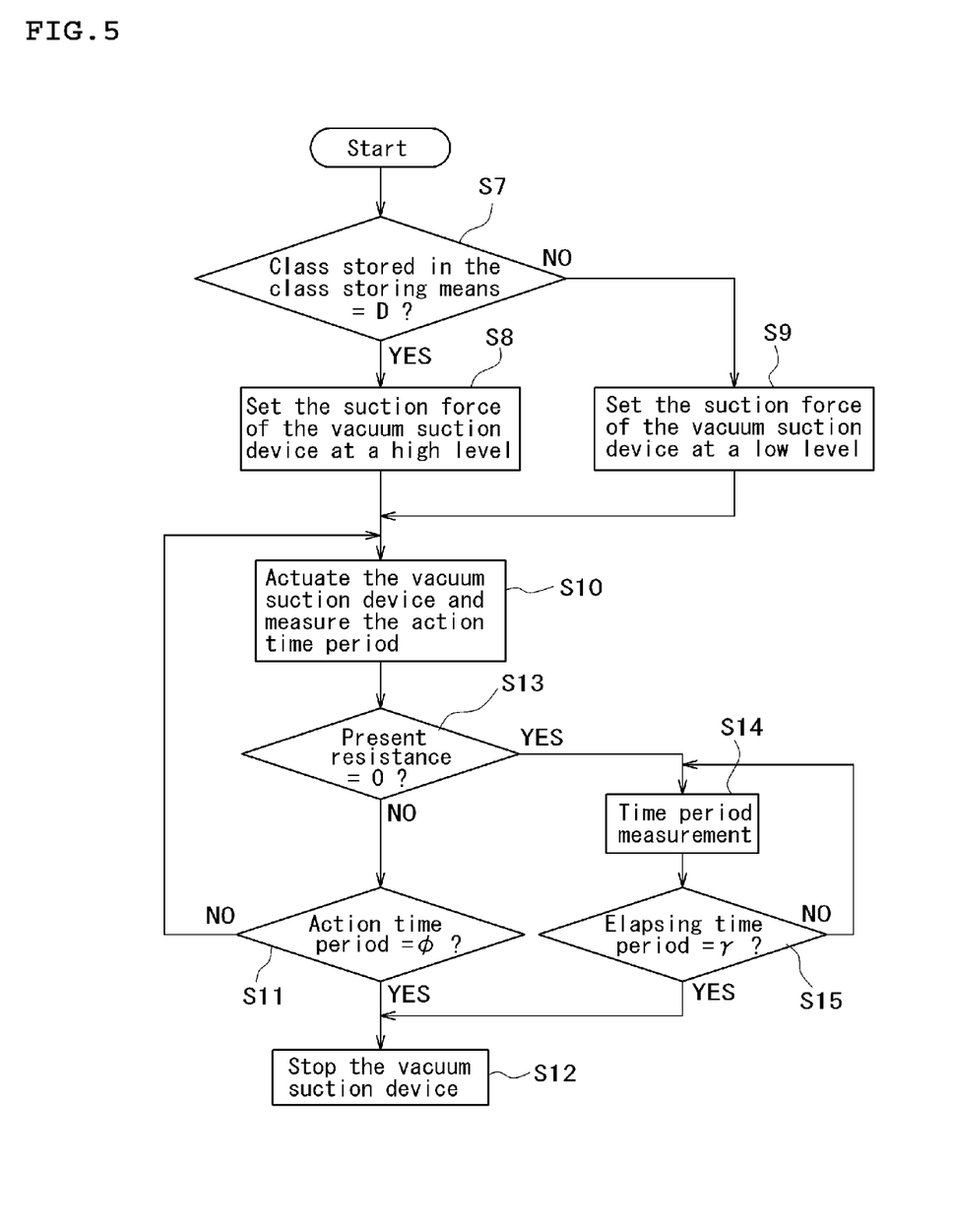
FIG. 5 is a flowchart showing another example of the flow of control in the manual operation-based action mode.

FIG. 5 shows another example of the flow of control in the manual operation-based action mode (S2), and since the flow from step S7 to step S10 is the same as that of FIG. 4, the same symbols are used to avoid duplicate explanation. Further, the steps corresponding to the steps in the flow of FIG. 4 are also given the same symbols.

In this flow of control, shifting from step S10 in which the vacuum suction device 9 is actuated while the action time period is measured, to step S13 occurs, and at step S13 the present resistance of the state detection circuit 14 is referred to for judging whether or not the manual operation switch 13 has been turned on again. On the basis of the result of the judgment, either of alternatives is selected in control flow.

In the state where the manual operation switch 13 is turned off, the resistance is not 0. Therefore, shifting from step S13 to step S11 occurs, and at the time point when the action time period has exceeded the set time period $\phi$, shifting to step S12 occurs to stop the vacuum suction device 9 as in the flow of FIG. 4.

On the other hand, if the resistance is 0, it is judged that the manual operation switch 13 has been turned on, and shifting to step S14 occurs to start time period measurement. Then, at step S15, the elapsing time period is judged. That is, till the elapsing time period reaches $\gamma$, the processing of steps S14 and S15 is repeated, and if it is judged at step S15 that the elapsing time period has reached $\gamma$, shifting to step S12 occurs to stop the vacuum suction device 9, for terminating the manual operation-based action mode (S2). This flow of control is shown in the time charts of FIGS. 11 and 12. After completion of the mode, as shown in FIG. 3, shifting to step S1 occurs, and the observation of the resistance of the state detection circuit 14 is continued in the standby state.

In the flow of control shown in FIG. 5 described above, the operation of turning on the manual operation switch 13 again after start of action can be used as a urination end signal. That is, if the manual operation switch 13 is turned on before urination and is turned on again during urination, the action of the vacuum suction device 9 can be stopped after the lapse of $\gamma$ seconds from the time point when the switch is turned on second time. Therefore, if the second operation of turning on the manual operation switch 13 is performed at the time point when urination ends, the action of the vacuum suction device 9 can be stopped after the lapse of the set time period $\gamma$, i.e., a sufficient time period for discharging all urine into the urine tank 8 after completion of urination.

In this configuration, in the case where urination is completed in a very short time shorter than the abovementioned set time period $\phi$, if the manual operation switch 13 is turned on second time, the action of the vacuum suction device 9 can be stopped at a time point earlier than the time point when the predetermined time period $\phi$ has elapsed. Therefore, the wasteful action of the vacuum suction device 9 can be prevented.

Figure 6:
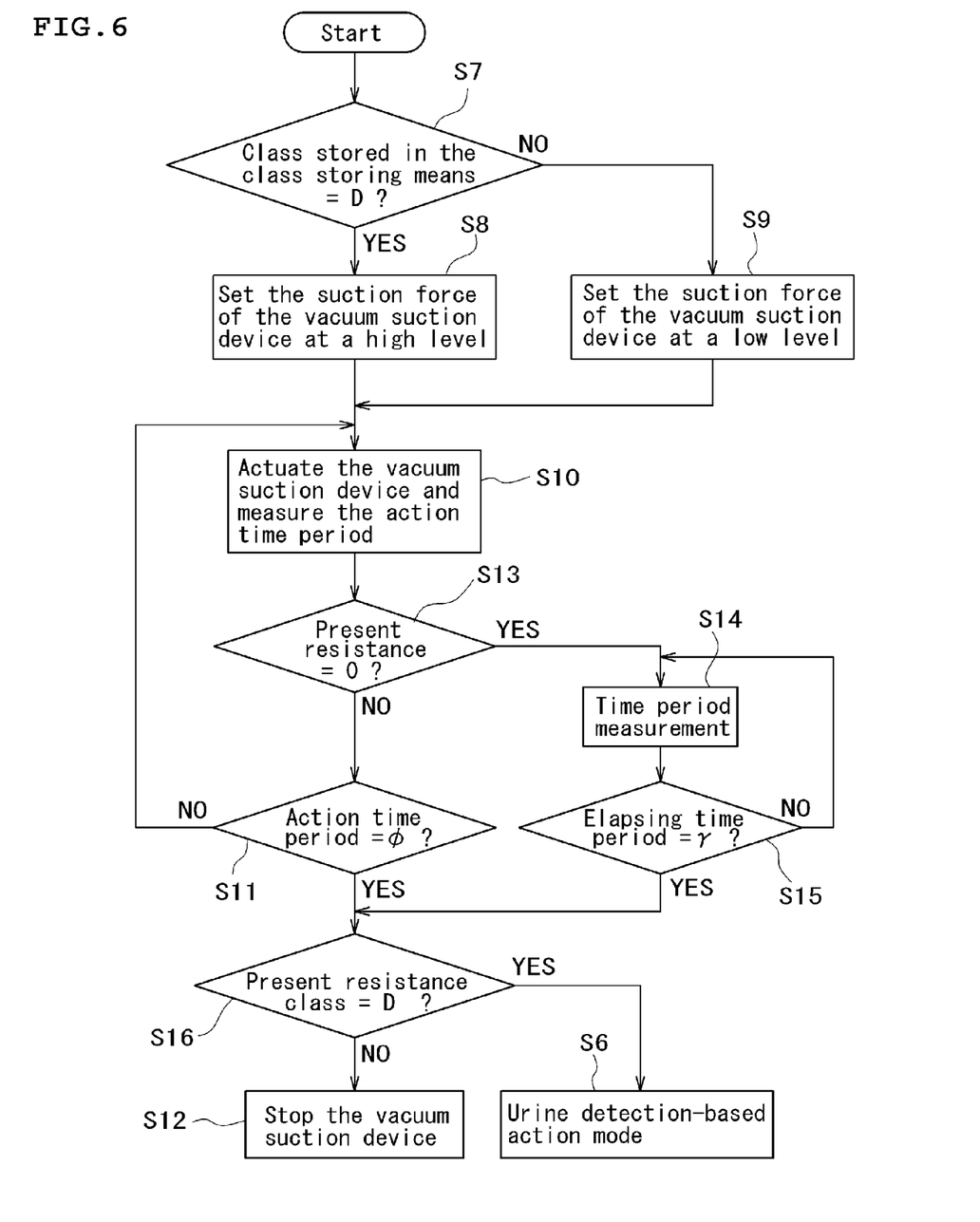
FIG. 6 is a flowchart showing a further other example of the flow of control in the manual operation-based action mode.

FIG. 6 shows a further other example of the flow of control in the manual operation-based action mode (S2), and since the flow from step S7 to step 11 and to step S15 is the same as that of FIG. 5, the same symbols are used to avoid duplicate explanation. Further, the steps corresponding to the steps in the flow of FIG. 5 are also given the same symbols.

In this flow of control, after the lapse of the action time period $\phi$ at step S11 or the elapsing time period $\gamma$ at step S15 and before the vacuum suction device 9 is stopped at step S12, whether or not the present resistance class is class D is judged at step S16. If the resistance class is not class D but is class A, B or C, shifting to step S12 occurs to stop the vacuum suction device 9, for terminating the manual operation-based action mode (S2) as in the flow of FIG. 4 or 5. After completion of the mode, as described above, shifting to step S1 occurs, and the observation of the resistance of the state detection circuit is continued as shown in FIG. 3.

On the other hand, if the resistance class is judged to be class D at step S16, shifting to the urine detection-based action mode (S6) shown as step S6 occurs, and the control in the urine detection-based action mode (S6) is performed. The flow of control in the urine detection-based action mode is described later.

In this flow of control, in the control action of manual operation-based action mode (S2), in the case where the resistance between the electrodes is re-conformed and found to be equivalent to the urination-detected state before the vacuum suction device 9 is stopped, shifting to the urine detection-based action mode (S6) can occur. Therefore, in the case where the urination time period is elongated unexpectedly, the urine can be reliably discharged into the urine tank 8.

Figure 7:
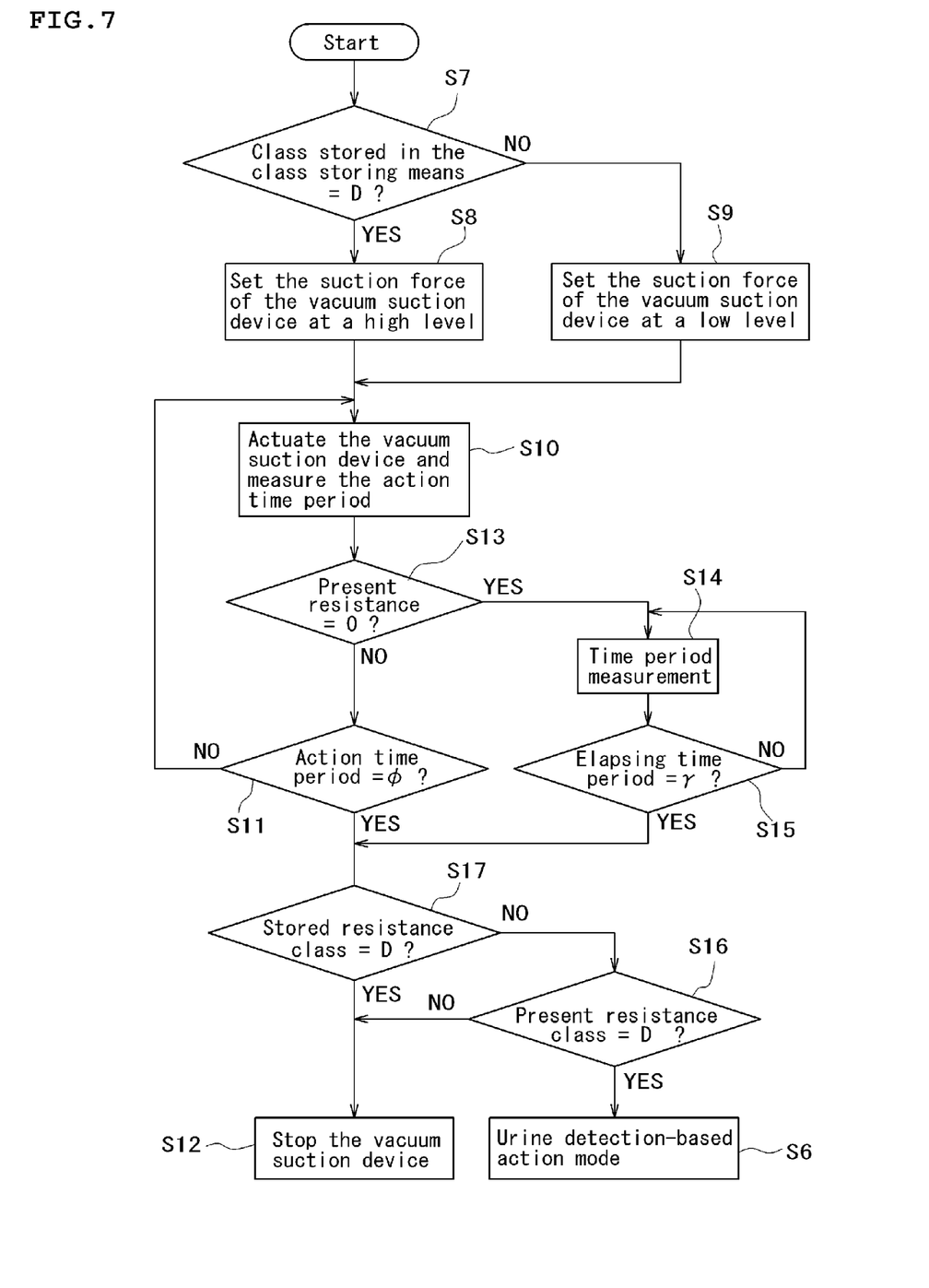
FIG. 7 is a flowchart showing a further other example of the flow of control in the manual operation-based action mode.

FIG. 7 shows a further other example of the flow of control in the manual operation-based action mode (S2), and since the flow from step S7 to step S11 and to step S15 is the same as that of FIG. 6, the same symbols are used to avoid duplicate explanation. Further, the steps corresponding to the steps in the flow of FIG. 6 are also given the same symbols.

In this flow of control, after the lapse of the action time period $\phi$ at step S11 or the elapsing time period $\gamma$ at step S15 and before shifting to step S16 occurs for judging whether or not the present resistance class is class D, shifting to step S17 occurs for judging whether or not the stored resistance class is class D.

In the case where the stored resistance class is judged to be class D at step S17, it is judged that the present resistance class must be class D even without confirming it, and shifting to step S12 occurs to stop the vacuum suction device 9, for terminating the manual operation-based action mode (S2). After completion of the mode, as described above, shifting to step S1 occurs, and the observation of the resistance of the state detection circuit is continued as shown in FIG. 3.

On the other hand, in the case where the stored resistance class is judged to be other than class D, i.e., class A, B or C at step S17, shifting to step S16 occurs to judge whether or not the present resistance class is class D.

If the present resistance class is other than class D, it means that there is no urine existing between the electrodes, and therefore shifting from step S16 to step S12 occurs to stop the vacuum suction device, for terminating the manual operation-based action mode.

On the other hand, if the present resistance class is judged to be class D at step S16, it means that the class has been changed from a class other than class D to the present class D. Consequently it is highly probable that urine exists between the electrodes, and therefore in this case, shifting from step S16 to the urine detection-based action mode at step S6 occurs, and control in the urine detection-based action mode (S6) is performed.

In this flow of control, in the case where the stored resistance class is class D even if the present resistance class is class D, it can be estimated that the present class D may not be attributable to the detection of urine since the manual operation-based action mode (S2) is active. Further, if shifting to the urine detection-based action mode (S6) occurs, the vacuum suction device 9 cannot be stopped. Therefore, it can be prevented that the action of the vacuum suction device 9 is continued more than necessary.

Figure 8:
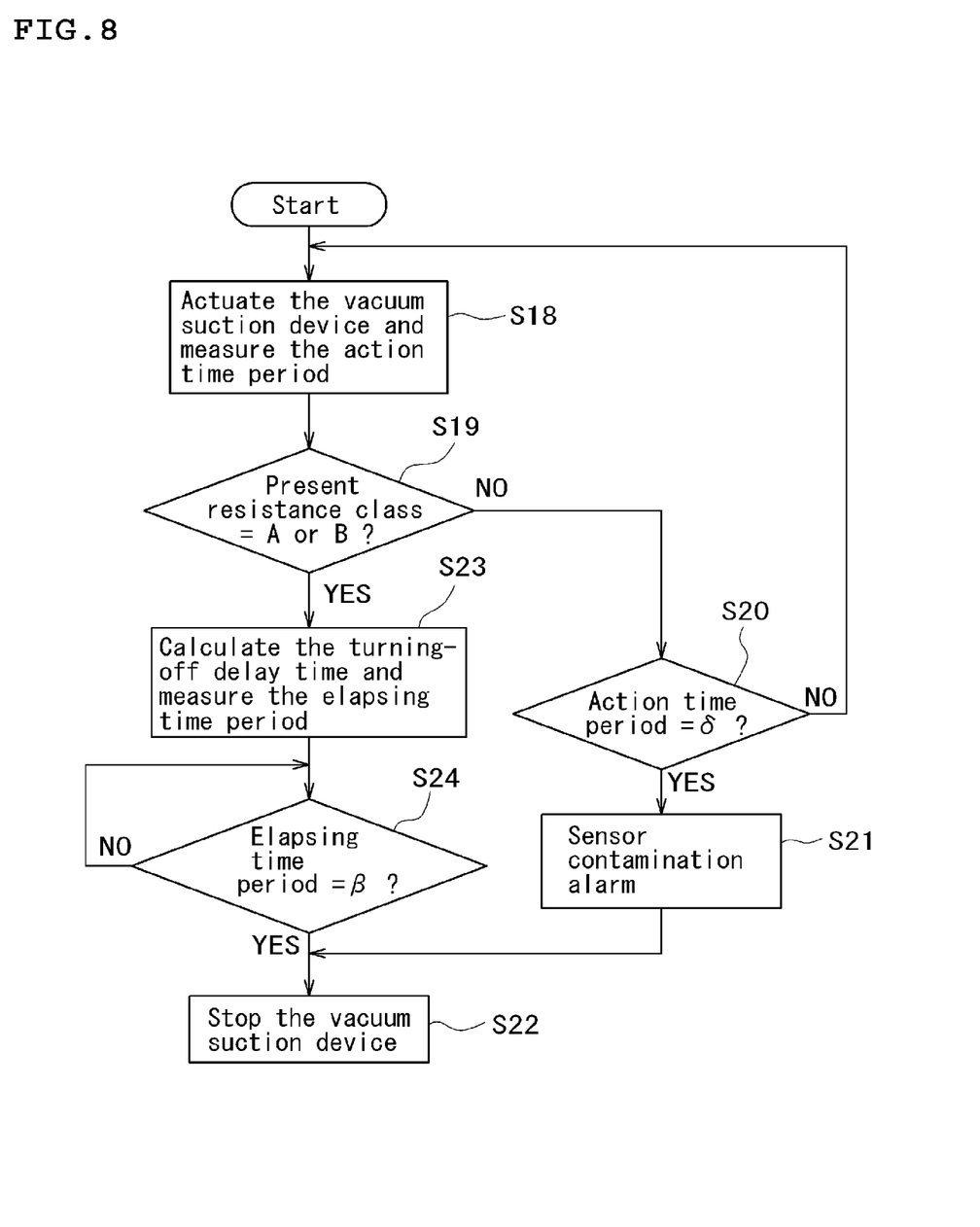
FIG. 8 is a flowchart showing an example of the flow of control in the urine detection-based action mode.
Figure 9:
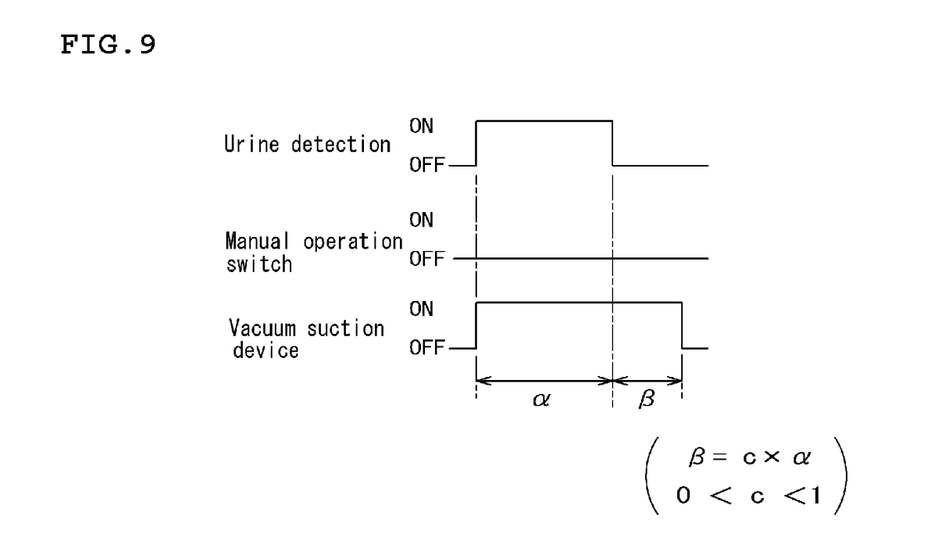
FIG. 9 is a time chart showing a part of the flow of control.

FIG. 8 shows an example of the flow of control in the urine detection-based action mode (S6). If shifting from step S4 to the urine detection-based action mode at step S6 occurs in FIG. 3, the vacuum suction device 9 is actuated and the action time period is measured at first at step S18.

Then, shifting to step S19 occurs, and whether or not the present resistance class is class A or B is judged.

If the present resistance class is neither class A nor class B, i.e., is class C or D at step S19, it is judged that urine exists between the electrodes still now, and shifting to step 20 occurs. At step 20, if it is judged that the action time period does not reach δ, shifting to step S18 occurs to continue the action of the vacuum suction device 9 and the measurement of action time period.

In the case where the action time period of the vacuum suction device 9 reaches δ, the supposed urination time period is greatly exceeded. Therefore, in the case where it is judged that the action time period reaches δ at step S20, shifting to step S21 occurs to issue a sensor contamination alarm, and shifting to step S22 occurs to stop the vacuum suction device 9.

On the other hand, at step S19, in the case where the present resistance class is judged to be class A or B, there is no urine existing between the electrodes, that is, urination ends. Therefore, shifting from step S19 to step S23 occurs to calculate the turning-off delay time period β, and the elapsing time period for the turning-off delay time period is measured.

The turning-off delay time period β is, as described above, set by multiplying the action time period α of the vacuum suction device 9 till the time point when shifting to step S23 occurs, by coefficient c smaller than 1 such as ½, from formula β=c×α, so that all the urine in the urine transport tube can be reliably discharged into the urine tank 8 and so that the vacuum suction device 9 can be prevented from being actuated for a time period longer than necessary. This flow of control is shown in the time chart of FIG. 9.

After the turning-off delay time period β is calculated at step S23, shifting to step S24 occurs to judge whether or the turning-off delay time period β has elapsed, and after the lapse of the turning-off delay time period β, shifting to step S22 occurs to stop the vacuum suction device 9, for terminating the control in the urine detection-based action mode (S6).

In this flow of control, at step S19, only in the case where the present resistance class is class A or B, it is judged that there is no urine existing between the electrodes, and after the lapse of the set time period β, the vacuum suction device 9 is stopped. In the case where the present resistance class is class C, the action of the vacuum suction device 9 is continued, to ensure that no existence of urine between the electrodes can be reliably detected. Another example of control can be such that also in the case of class change from class D to class C, it can be judged that there is no urine existing between the electrodes.

INDUSTRIAL APPLICABILITY

The present invention as described above can provide a vacuum suction type urine collector which allows urine to be reliably collected irrespective of how far the user is confident of the reliability of the vacuum suction type urine collector, and therefore the vacuum suction type urine collector is most suitable for use not only in a hospital or the like but also in a household, etc.

The invention claimed is:

1. A control system for a vacuum suction type urine collector, the vacuum suction type urine collector including a urine receiver, a urine tank, a urine transport tube defining a vacuum suction urine path extending from the urine receiver to the urine tank, and a vacuum suction device for providing vacuum suction, said control system comprising:
 a pair of electrodes for being installed on a side of the urine receiver;
 a detection resistor connected in series to said pair of electrodes to form a series circuit;
 a manual operation switch connected in parallel to said series circuit to form a state detection circuit; and
 a controller which measures resistance between said pair of electrodes to automatically detect urine,
 wherein said controller is configured to:
 measure the resistance of said state detection circuit,
 classify the measured resistance of said state detection circuit as one of several established resistance classes,
 store the classified resistance class,
 detect a change of class by comparing the classified resistance class with the corresponding stored resistance class,
 set an action mode in reference to the detected change of class and to a state of said manual operation switch detected from the resistance of said state detection circuit, and
 control the vacuum suction device on the basis of the set action mode,
 wherein the action mode is set to one of:
 (i) a manual operation-based action mode where said manual operation switch is turned on; and
 (ii) a urine detection-based action mode where said manual operation switch is turned off,
 wherein said set action mode sets the manual operation-based action mode when the resistance of the state detection circuit is zero,
 wherein the several established resistance classes include a normal class of a high resistance range corresponding to a state substantially free from contamination between said electrodes, an alarm class of a low resistance range corresponding to a state where it is difficult to detect urine in reference to the resistance because of the contamination between said electrodes, and an intermediate class corresponding to the state between the normal class and the alarm class,
 wherein said set action mode sets the urine detection-based action mode when the change from another class to the alarm class is detected, and cancels the urine detection-based action mode when the change from the alarm class to another class is detected, for actuating said control of the vacuum suction device, wherein said control of the vacuum suction device stops the action of the vacuum suction device and issues an alarm if the alarm class is detected after an elapsing time period ($\alpha$) from the time point when the urine detection-based action mode is set has exceeded a set time period ($\delta$), and wherein, after issuing the alarm, said control of the vacuum suction device activates the vacuum suction device when said manual operation switch is turned on.

2. The control system of claim 1, wherein said control of the vacuum suction device issues a contamination alarm in the case where the resistance class is identified while the power of the urine collector is switched on is the alarm class.

3. The control system of claim 1, wherein the control of the vacuum suction device stops the action of the vacuum suction device after the lapse of a set time period ($\beta$) from the time point when the urine detection-based action mode is cancelled.

4. The control system of claim 3, wherein the set time period ($\beta$) is set as a coefficient multiple of the elapsing time period ($\alpha$) from the time point when the urine detection-based action mode is set to the time point when the urine detection-based action mode is cancelled.

5. A control system for a vacuum suction type urine collector, the vacuum suction type urine collector including a urine receiver, a urine tank, a urine transport tube defining a vacuum suction urine path extending from the urine receiver to the urine tank, and a vacuum suction device for providing vacuum suction, said control system comprising:
   a pair of electrodes for being installed on a side of the urine receiver;
   a detection resistor connected in series to said pair of electrodes to form a series circuit;
   a manual operation switch connected in parallel to said series circuit to form a state detection circuit; and
   a controller which measures resistance between said pair of electrodes to automatically detect urine,
   wherein said controller is configured to:
   measure the resistance of said state detection circuit,
   classify the measured resistance of said state detection circuit as one of several established resistance classes,
   store the classified resistance class,
   detect a change of class by comparing the classified resistance class with the corresponding stored resistance class,
   set an action mode in reference to the detected change of class and to a state of said manual operation switch detected from the resistance of said state detection circuit, and
   control the vacuum suction device on the basis of the set action mode,
   wherein the action mode is set to one of:
   (i) a manual operation-based action mode where said manual operation switch is turned on; and
   (ii) a urine detection-based action mode where said manual operation switch is turned off,
   wherein said set action mode sets the manual operation-based action mode when the resistance of the state detection circuit is zero,
   wherein the several established resistance classes include a normal class of a high resistance range corresponding to a state substantially free from contamination between said electrodes, an alarm class of a low resistance range corresponding to a state where it is difficult to detect urine in reference to the resistance because of the contamination between said electrodes, and an intermediate class corresponding to the state between the normal class and the alarm class,
   wherein said set action mode sets the urine detection-based action mode when the change from another class to the alarm class is detected, and cancels the urine detection-based action mode when the change from the alarm class to another class is detected, for actuating said control of the vacuum suction device,
   wherein said control of the vacuum suction device stops the action of the vacuum suction device and issues an alarm if the alarm class is detected after an elapsing time period ($\alpha$) from the time point when the urine detection-based action mode is set has exceeded a set time period ($\delta$), and
   wherein, after issuing the alarm, said control of the vacuum suction device activates the vacuum suction device when said manual operation switch is turned on, and
   wherein the control of the vacuum suction device stops the action of the vacuum suction device after the lapse of a set time period ($\phi$) from the time point when the manual operation-based action mode is set with said manual operation switch turned on.

6. The control system of claim 5, wherein the control of the vacuum suction device stops the action of the vacuum suction device, after the lapse of a set time period ($\gamma$) from the time point when said manual operation switch is turned on again, in the case where said manual operation switch is turned on again before the set time period ($\phi$) elapses from the time point when the manual operation-based action mode is set with said manual operation switch turned on.

7. The control system of claim 6, wherein said control of the vacuum suction device refers to the class of the resistance of said state detection circuit at the time point when the set time period ($\gamma$) has elapsed, and said set action mode sets the action mode to the urine detection-based action mode if the class is the alarm class, and if the class is other than the alarm class, the vacuum suction device is stopped.

8. The control system of claim 6, wherein at the time point when the set time period ($\gamma$) has elapsed, said control of the vacuum suction device refers to the class of the resistance of said state detection circuit at that time and to the stored resistance class, and
   (i) in the case where the stored resistance class is the alarm class the vacuum suction device is stopped, and
   (ii) in the case where the stored resistance class is other than the alarm class, said set action mode sets the action mode to the urine detection-based action mode if the resistance class at that time is the alarm class, and the vacuum suction device is stopped if the resistance class at that time is other than the alarm class.

9. The control system of claim 1, wherein in the urine detection-based action mode, said control of the vacuum suction device actuates the vacuum suction device in such a manner as to make the suction force high, and
   wherein in the manual operation-based action mode, said control of the vacuum suction device actuates the vacuum suction device in such a manner as to make the suction force lower than that in the urine detection-based action mode.

10. The control system of claim 9, wherein in the manual operation-based action mode, said control of the vacuum suction device actuates the vacuum suction device in such a manner as to make the suction force high in the case where the immediately preceding resistance class is the alarm class.

* * * * *